United States Patent [19]

Ittah et al.

[11] Patent Number: 5,432,415
[45] Date of Patent: Jul. 11, 1995

[54] AUTOMATICALLY CONTROLLED CLEANING ARRANGEMENT IN PARTICULAR FOR A VEHICLE WINDSHIELD

[75] Inventors: Benjamin Ittah, Chêne-Bougeries/Gen e,gra e ve, Switzerland; Louis Béchet, Sciez, France; Marcel Arditi, Genève, Switzerland

[73] Assignee: SMH Management Services AG, Biel, Switzerland

[21] Appl. No.: 193,006

[22] PCT Filed: Jun. 22, 1993

[86] PCT No.: PCT/CH93/00160
§ 371 Date: Feb. 16, 1994
§ 102(e) Date: Feb. 16, 1994

[87] PCT Pub. No.: WO94/00319
PCT Pub. Date: Jan. 6, 1994

[30] Foreign Application Priority Data
Jun. 23, 1992 [FR] France ............... 92 07773

[51] Int. Cl.⁶ ................................. B60S 1/08
[52] U.S. Cl. .................... 318/483; 318/444; 318/460; 318/DIG. 2
[58] Field of Search ............... 318/608, 643, 443, 444, 318/460, 483, DIG. 2; 15/250.12, 250.13, 250.14, 250.17

[56] References Cited

U.S. PATENT DOCUMENTS

| 4,180,886 | 1/1980 | Scherz . | |
|---|---|---|---|
| 4,542,325 | 9/1985 | Kobayashi et al. . | |
| 4,613,802 | 9/1986 | Kraus et al. | 318/483 |
| 4,768,256 | 9/1988 | Motoda . | |
| 5,015,931 | 5/1991 | Muller | 318/483 |
| 5,203,207 | 4/1993 | Sugiyama | 73/170.17 |
| 5,266,873 | 11/1993 | Arditi et al. . | |

FOREIGN PATENT DOCUMENTS 0512653 11/1992 European Pat. Off. .

OTHER PUBLICATIONS

Soviet Inventions Illustrated; Section EI, Week E09, 14 Apr. 1982 Derwent Publications Ltd., London, GB; Class X22, AN C4732 E/09 & SU,A,833 463 (Aleksandrov V V) 6 Jun. 1981.

*Primary Examiner*—Bentsu Ro
*Attorney, Agent, or Firm*—Griffin, Butler, Whisenhunt & Kurtossy

[57] ABSTRACT

An automatically controlled cleaning device (14) for removing visibility-impairing foreign matter, e.g. rain, snow or mud, from the surface of a window such as a motor vehicle windscreen (8). The device uses a sensor such as an ultrasonic transducer (12a, 12b) in which the frequency (f) and the spacing (d) between the transmitter (12a) and the receiver (12b) enable the presence of foreign matter to be detected simply by measuring the phase difference between the transmitted signal and the received signal. This device may be used in automatic wiper systems or the like.

8 Claims, 2 Drawing Sheets

AUTOMATICALLY CONTROLLED CLEANING ARRANGEMENT IN PARTICULAR FOR A VEHICLE WINDSHIELD

FIELD OF THE INVENTION

The present invention concerns generally an automatically controlled cleaning arrangement intended for the elimination of foreign matter such as rain, snow or mud which hinders visibility from a glass surface such as a vehicle windshield and, more specifically, it concerns an arrangement of this type employing elastic waves in order to detect the presence of such foreign matter.

BACKGROUND OF THE INVENTION

Different methods for detecting the presence of foreign matter on a glass surface are known. In most cases, advantage is taken of the fact that the transmission of a wave (optical, elastic or other wave) in the material of the glass can be found to be noticeably affected by a modification of the medium in which the glass is located. Thus, in the case of a windshield for an automotive vehicle, the transmission of a luminous wave by multiple reflection in the thickness of the glass may be more or less attenuated as a function of the surface state of one of the boundary surfaces of the windshield.

French patent 2.648.096 proposes an automatic cleaning system using optical detection means applying this principle of attenuation.

This latter principle still remains valid in the case of an elastic wave and ultrasonic detection systems have often been proposed.

German patent DE 40 33 975, for example, detects the variations in amplitude of an ultrasonic signal received at a detector arranged at a certain distance from the transmitter.

An analogous principle of detection by amplitude variation is employed in the French patent 91 05784 in which the functions of transmission and reception are effected by one and the same transducer.

In Japanese patent application JP 59-192 651, it is the existence of supplemental pulses in the ultrasonic signal received by the detector which enables deduction of the presence of foreign bodies. Such additional pulses arise from the fact that the presence of foreign bodies generates supplemental wave transmission paths.

The known arrangements cited hereinabove employing an ultrasonic detection system nevertheless exhibit the drawback of operating at a relatively high frequency, typically on the order of 1 to 100 MHz; and whether such frequency be emitted as a continuous wave or in the form of pulses, the processing circuits must also be able to work at high frequency. This condition forbids envisaging for such applications the use of inexpensive circuits such as those formed with the help of slower technologies, for example MOS or CMOS technologies. Now it is readily conceived that a high cost of obtaining such circuits constitutes a brake on the generalization of use of such automatically controlled cleaning arrangements which represent however, for the user, an undeniable advantage as much in view of comfort as that of security.

Thus a purpose of the invention is to obtain an automatically controlled cleaning arrangement intended for the elimination of foreign matter from the surface of a glass using an ultrasonic detector and not showing the drawbacks mentioned hereinabove.

Another purpose of the invention is to obtain a cleaning arrangement the detector of which functions at a relatively low frequency.

Still another purpose of the invention is to obtain a cleaning arrangement the cost of which is lower than that of systems of the prior art.

SUMMARY OF THE INVENTION

Such purposes can be attained thanks to the fact that it has been observed that, for a given frequency and distance between the transmitter and the receiver, the phase difference between the signal emitted by the transmitter and the signal received by the receiver can vary, in particular, as a function of the presence of foreign matter on the surface of the glass. This phenomenon is observed for an emitted signal frequency on the order of 100 kiloHertz.

The characteristics of the invention are defined in the attached claims.

Other purposes, characteristics and advantages of the present invention will appear more clearly upon reading the following description of an embodiment thereof, said description being intended to be purely illustrative and in relation with the attached drawings.

DESCRIPTION OF THE PREFERRED EMBODIMENT

The description of the present invention which follows will be established within the framework of an application for the elimination of moist foreign matter such as mud, rain, snow, etc. from the windshield of an automotive vehicle.

At the same time, it is self-evident that the invention is in no manner limited to this application and that it may be advantageously employed within the framework of any other cleaning application for a thin sheet formed of a material capable of transmitting an ultrasonic signal.

Figure 1:
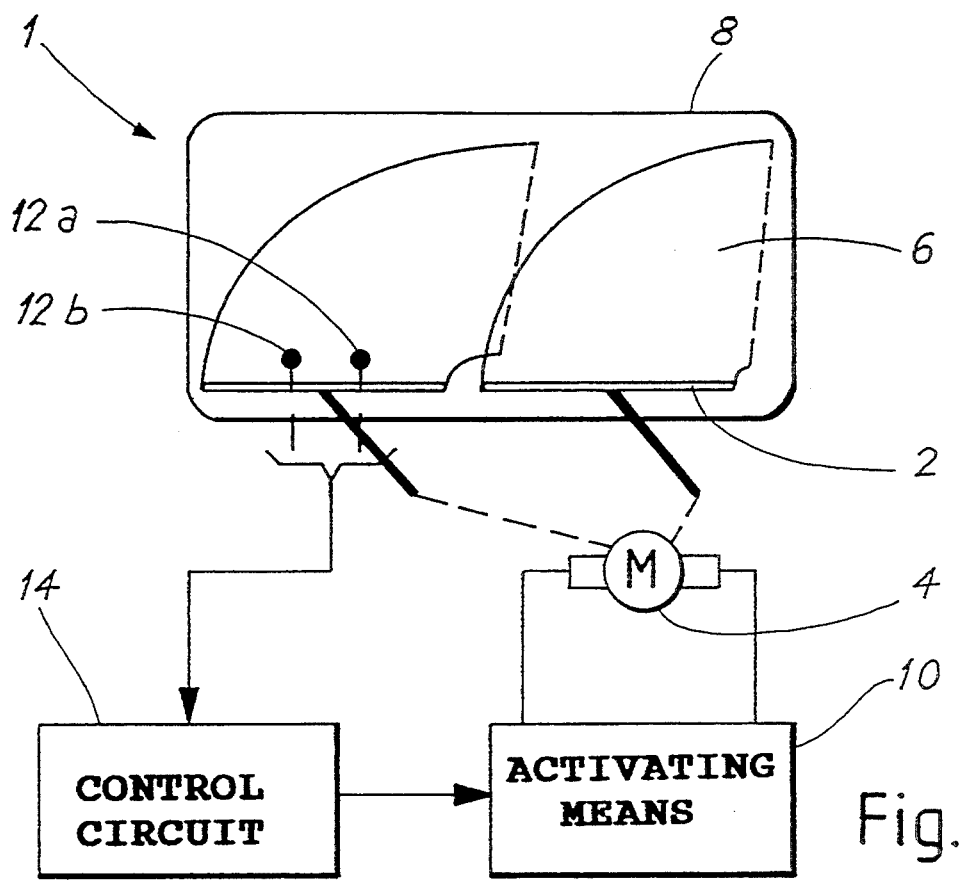
FIG. 1 shows a schematic of the principle of the arrangement of the invention.

Referring to FIG. 1, there is seen a standard arrangement for operating a windshield wiper designated by the general reference 1. Arrangement 1 comprises windshield wipers 2 mechanically coupled to a motor 4 such that when they are activated, they sweep a zone 6 in the form of a circular sector of a single layer windshield 8. Activating means 10 connected to motor 4 enable the placing in operation and/or stopping of such motor.

Figure 2:
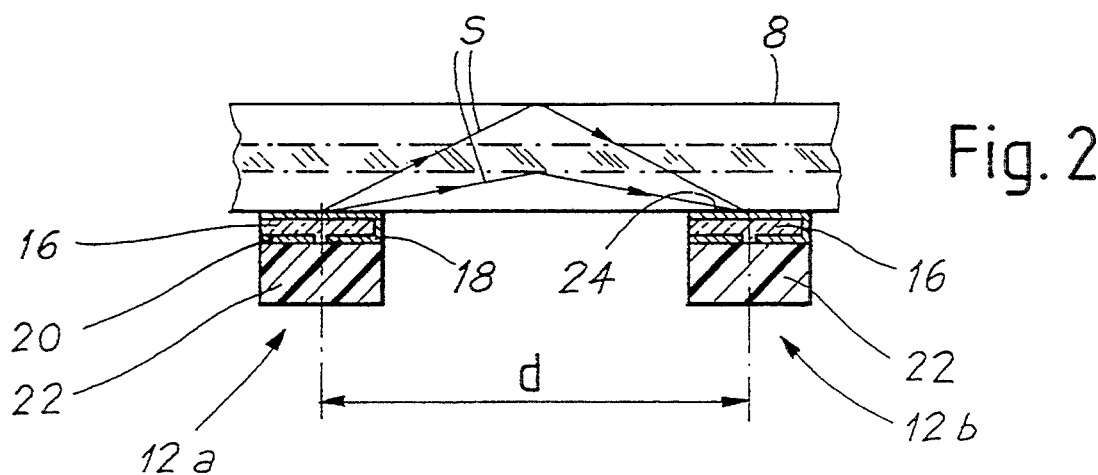
FIG. 2 is a partial cross-section showing the assembly of the piezoelectric transducers on the windshield.
Figure 3:
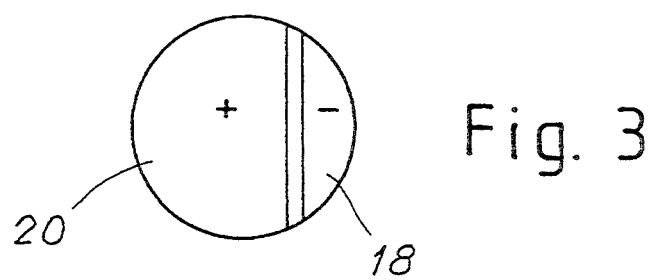
FIG. 3 shows a piezoelectric pellet provided with its electrodes.
Figure 4:
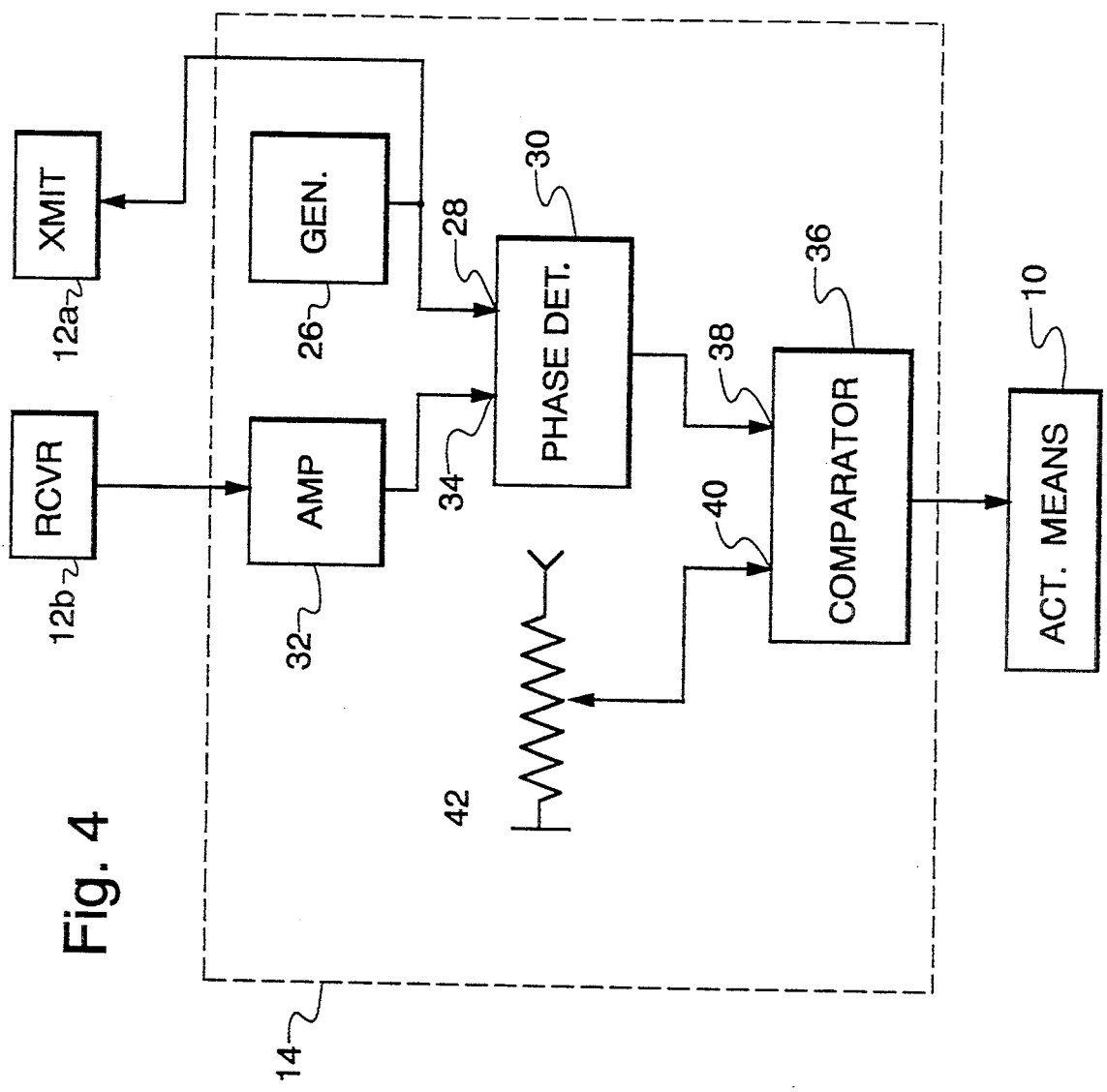
FIG. 4 shows a schematic block of the control circuit for the windshield wiper motor.

The automatic operation of windshield wipers according to the invention is brought about with the help of electrosonic detection means 12a and 12b placed against the windshield facing zone 6 and from a control circuit 14, the function and structure of which are described in relation with FIGS. 2 to 4.

Referring now to FIGS. 2 and 3, there will be seen respectively the positioning of transducers 12a and 12b on the windshield 8 as well as the form of the electrodes of transducers 12a, 12b.

The transducers, whether they be used in transmission or reception, are identical. Transducers 12a, 12b comprise a piezoelectric element 16, electrodes 18, 20 as well as damping means 22. They are secured onto the interior face of windshield 8 by means of a thin film of glue 24 represented by a stroke on FIG. 2. The two transducers 12a, 12b are separated by a distance d the determination of the value of which will be explained subsequently.

Transducers 12a, 12b may be made in the form of pellets of a piezoelectric material such as PZT, lithium niobate, lead titanate, etc. Each transducer 12a, 12b comprises a first electrode 18 (for instance negative) which extends on the one hand over its entire face which is in contact with the windshield 8 and, on the other hand, on a portion of the opposite face (FIG. 3). These transducers 12a, 12b each comprise a second electrode 20 (positive) insulated from the first electrode 18 and which covers over the portion of said opposite face not covered over by the first electrode 18.

The electrodes are formed by known means, such as the deposition and chemical engraving of a metal or of a metallic alloy (nickel, silver, etc.). The damping means 22 are assembled in an appropriate manner on the piezoelectric element 16. The role of such damping means 22 is, on the one hand, to confine the mechanical and vibration energy in the desired direction (that is to say, towards the windshield) and, on the other hand, to attenuate the reflected interference vibrations of the signal transmitted and/or received by the transducers.

Information on the constitution and assembly of such damping means 22 may be found respectively in the article of Y. Bar-Cohen et al. appearing in the review J. Acoustic Am. Vol. 75, Nr. 5, May 1984 on pages 1629 et following and in the French patent application 91 05784.

FIG. 4 shows the block schematic of the control circuit 14 of the cleaning arrangement of the invention. Circuit 14 comprises a generator 26 for a periodic signal having the desired frequency (see after). Generator 26 is coupled, on the one hand, to the transmitting transducer 12a and, on the other hand, to the input 28 of a phase detection circuit 30. An amplifier 32 which receives as an input the signal provided by transducer 12b provides an amplified signal at a second input 34 of the phase detection circuit 30. A comparator circuit 36 receives on a first input 38 the output signal of said phase detection circuit 30. Its second input 40 is coupled to means 42 for setting a threshold value. The output of the comparator circuit controls the activating means 10 of the windshield wiper motor 4.

The principle of operation of the arrangement is as follows. Thus, as has been said hereinabove, there exists for a given windshield a correlation between the frequency (f) of the signal and the distance (d) between the transmitter and the receiver for which the phase difference between the emitted signal and the received signal varies considerably as a function of the surface state of the windshield. The frequency is on the order of 100 to 150 kiloHerz and the distance d on the order of 10 to 20 millimeters. It will be noted that the dimensions have been highly exaggerated on the drawing for reasons of clarity. The exact values of the frequency and of the distance depend on the constitution (material, mono- or multilayer, etc.) and on the thickness of the windshield and also on those of the transducers. The determination of the couple (f)/(d) may be obtained in an empirical manner. For that it is necessary to have available a generator for variable frequencies covering the range from 100 to 150 kiloHertz and adjustement means for the distance d. Such phase difference is that which exists between the emitted wave and the resulting wave detected by the receiver.

The waves which are propagated between the transmitter and the receiver are subject to multiple reflections and trace different trajectories, certain of which have been shown by S on FIG. 2. Some of these waves are influenced by the presence of water, for example by a modification of the amplitude thereof. Certain other waves are not influenced, as for example the direct wave or again the wave which is propagated in the interior sheet of a layered windshield.

The received signal is determined by the vector sum of the different acoustic waves which are propagated between the transmitter and the receiver.

The adjustment consists in selecting a pair frequency—distance which in the vector sum renders preponderant the participation of waves sensitive to the presence of water on the outer surface of the windshield.

If reference is made to the schematic drawing of FIG. 4, generator 26 emits a continuous electrical signal at the desired frequency which is applied to the electrodes of transducer 12a. This latter generates an elastic vibration of the same frequency which is transmitted to the windshield on which it is secured. Transducer 12b transforms the received vibration into an electrical signal which, following amplification, is applied to the phase detector 30. Such phase detector furnishes at its output a signal representing the phase difference existing between the signal emitted by generator 26 and the signal issuing from amplifier 32. If the value of the phase difference exceeds a threshold value determined by means 42 (the value of the threshold may be determined in an empirical manner according to the determination of the frequency and distance d), the output of comparator 36 changes its logic state and operates the activator 10 of the windshield wiper motor. It is evident that in place of an order "all or nothing" for the windshield wiper motor, one could have the speed of such motor depend on the signal representing the phase difference which is of an analog nature. Thus, the speed of the motor would be directly related with the quantity of impurities (rain, snow, mud, etc.) on the surface of the windshield.

Although the present invention has been described within the framework of a specific embodiment, it is however clear that it is not limited to such example and that it is capable of modifications or variants without departing from its domain.

We claim:

1. Automatically controlled cleaning arrangement intended for the elimination of moist foreign bodies from a glass surface and comprising cleaning means for said surface, activating means for said cleaning means, means for detecting the presence of foreign bodies with the help of an ultrasonic transmitter and receiver arranged on the glass in order to furnish a detection signal representing such presence and control means for operating said activating means in response to the detection signal, characterized in that the frequency (f) of the signal emitted by the transmitter and the distance (d) existing between the transmitter and the receiver are selected in a manner such that the phase difference between said emitted signal and the signal received by the receiver is a maximum in the presence of foreign bodies and in that said control means includes a circuit for measuring said phase difference.

2. Automatically controlled cleaning arrangement according to claim 1 characterized in that said signal emitted by the transmitter is a continuous wave signal.

3. Automatically controlled cleaning arrangement according to claim 1 characterized in that the frequency of the emitted signal is comprised between 100 and 150 kiloHertz and in that the distance between the transmitter and the receiver is comprised between 10 and 12 millimeters.

4. Automatically controlled cleaning arrangement according to any of claims 1 to 3 characterized in that said transmitter and said receiver are piezoelectric transducers.

5. Automatically controlled cleaning arrangement according to claim 4 characterized in that said control means comprise:
- a generator for generating electrical signals at the frequency f, the output of which is applied to said transmitter;
- an amplifier for amplifying the signal furnished by said receiver;
- a circuit for measuring the phase difference between the signal furnished by said generator and the signal furnished by said amplifier; and
- a comparator circuit for comparing the value of said phase difference with a threshold value and operating said activating means whenever said phase difference is greater than said threshold value.

6. Automatically controlled cleaning arrangement according to claim 2 characterized in that the frequency of the emitted signal is comprised between 100 and 150 kiloHertz and in that the distance between the transmitter and the receiver is comprised between 10 and 20 millimeters.

7. Automatically controlled cleaning arrangement according to claim 3 characterized in that said control means comprise:
- a generator for generating electrical signals at the frequency f, the output of which is applied to said transmitter;
- an amplifier for amplifying the signal furnished by said receiver;
- a circuit for measuring the phase difference between the signal furnished by said generator and the signal furnished by said amplifier; and
- a comparator circuit for comparing the value of said phase difference with a threshold value and operating said activating means whenever said phase difference is greater than said threshold value.

8. Automatically controlled cleaning arrangement according to claim 1 characterized in that said control means comprise:
- a generator for generating electrical signals at the frequency f, the output of which is applied to said transmitter;
- an amplifier for amplifying the signal furnished by said receiver;
- a circuit for measuring the phase difference between the signal furnished by said generator and the signal furnished by said amplifier; and
- a comparator circuit for comparing the value of said phase difference with a threshold value and operating said activating means whenever said phase difference is greater than said threshold value.

* * * * *